United States Patent
Dickey, Sr.

(10) Patent No.: US 6,353,031 B1
(45) Date of Patent: Mar. 5, 2002

(54) PAIN RELIEF PREPARATION FOR USE WHILE BATHING

(76) Inventor: James L. Dickey, Sr., 7809 Linda Vista Rd., Houston, TX (US) 77028

( * ) Notice: Subject to any disclaimer, the term of this patent is extended or adjusted under 35 U.S.C. 154(b) by 0 days.

(21) Appl. No.: 09/595,465

(22) Filed: Jun. 16, 2000

(51) Int. Cl.[7] .......................... A61K 35/78; A61K 9/46; A61K 33/10; A61K 33/14; A61K 29/00
(52) U.S. Cl. .................. 514/783; 424/466; 424/697; 424/717; 424/722; 424/400; 424/489
(58) Field of Search ................................ 424/466, 697, 424/195.1, 717, 722, 400, 489; 514/783

(56) References Cited

U.S. PATENT DOCUMENTS

| | | | |
|---|---|---|---|
| 4,368,134 A | 1/1983 | Kaeser | |
| 4,929,378 A | * 5/1990 | Morita et al. | 252/105 |
| 5,141,666 A | 8/1992 | Yorozu et al. | |
| 5,198,144 A | 3/1993 | Ichii et al. | |
| 5,370,867 A | * 12/1994 | Okawa et al. | 424/78.02 |
| 5,602,178 A | 2/1997 | Caroselli et al. | |
| 5,626,854 A | 5/1997 | Ichii et al. | |
| 5,656,200 A | 8/1997 | Boettcher et al. | |
| 5,958,462 A | * 9/1999 | Mclean | 424/630 |

* cited by examiner

Primary Examiner—Edward J. Webman
Assistant Examiner—Helen Nguyen

(57) ABSTRACT

A pain relief preparation for use while bathing for soothing and relaxing a user's body. The pain relief preparation for use while bathing includes (A) salts; (B) sodium bicarbonate; (C) an alkaline solution; (D) a bulb; and (E) aromatic seeds for use with water upon a user's body.

1 Claim, 2 Drawing Sheets

PAIN RELIEF PREPARATION FOR USE WHILE BATHING

BACKGROUND OF THE INVENTION

1. Field of the Invention

The present invention relates to a pain reliever and more particularly pertains to a new pain relief preparation for use while bathing for soothing and relaxing a user's body.

2. Description of the Prior Art

The use of a pain reliever is known in the prior art. More specifically, a pain reliever heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,368,134; 5,602,178; 5,198,144; 5,626,854; 5,141,666; and 5,656,200.

While these devices fulfill their respective, particular objectives and requirements, the aforementioned patents do not disclose a new pain relief preparation for use while bathing. The inventive preparation includes (A) salts; (B) sodium bicarbonate; (C) an alkaline solution; (D) a bulb; and (E) aromatic seeds for use with water upon a user's body.

In these respects, the pain relief preparation for use while bathing according to the present invention substantially departs from the conventional concepts and designs of the prior art, and in so doing provides an apparatus primarily developed for the purpose of soothing and relaxing a user's body.

SUMMARY OF THE INVENTION

In view of the foregoing disadvantages inherent in the known types of pain reliever now present in the prior art, the present invention provides a new pain relief preparation for use while bathing construction wherein the same can be utilized for soothing and relaxing a user's body.

The general purpose of the present invention, which will be described subsequently in greater detail, is to provide a new pain relief preparation for use while bathing which has many of the advantages of the pain reliever mentioned heretofore and many novel features that result in a new pain relief preparation for use while bathing which is not anticipated, rendered obvious, suggested, or even implied by any of the prior art pain reliever, either alone or in any combination thereof.

To attain this, the present invention generally comprises (A) salts; (B) sodium bicarbonate; (C) an alkaline solution; (D) a bulb; and (E) aromatic seeds for use with water upon a user's body.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new pain relief preparation for use while bathing which has many of the advantages of the pain reliever mentioned heretofore and many novel features that result in a new pain relief preparation for use while bathing which is not anticipated, rendered obvious, suggested, or even implied by any of the prior art pain reliever, either alone or in any combination thereof.

It is another object of the present invention to provide a new pain relief preparation for use while bathing which may be easily and efficiently manufactured and marketed.

It is a further object of the present invention to provide a new pain relief preparation for use while bathing which is of a durable and reliable construction.

An even further object of the present invention is to provide a new pain relief preparation for use while bathing which is susceptible of a low cost of manufacture with regard to both materials and labor, and which accordingly is then susceptible of low prices of sale to the consuming public, thereby making such pain relief preparation for use while bathing economically available to the buying public.

Still yet another object of the present invention is to provide a new pain relief preparation for use while bathing which provides in the apparatuses and methods of the prior art some of the advantages thereof, while simultaneously overcoming some of the disadvantages normally associated therewith.

Still another object of the present invention is to provide a new pain relief preparation for use while bathing for soothing and relaxing a user's body.

Yet another object of the present invention is to provide a new pain relief preparation for use while bathing which includes (A) salts; (B) sodium bicarbonate; (C) an alkaline solution; (D) a bulb; and (E) aromatic seeds for use with water upon a user's body.

Still yet another object of the present invention is to provide a new pain relief preparation for use while bathing that would provide instant relief from the pain of aching muscles and injuries to the neck, back, legs, feet, and other areas of the body.

Even still another object of the present invention is to provide a new pain relief preparation for use while bathing that would also help in the restoration and invigoration of a suer's skin tone.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
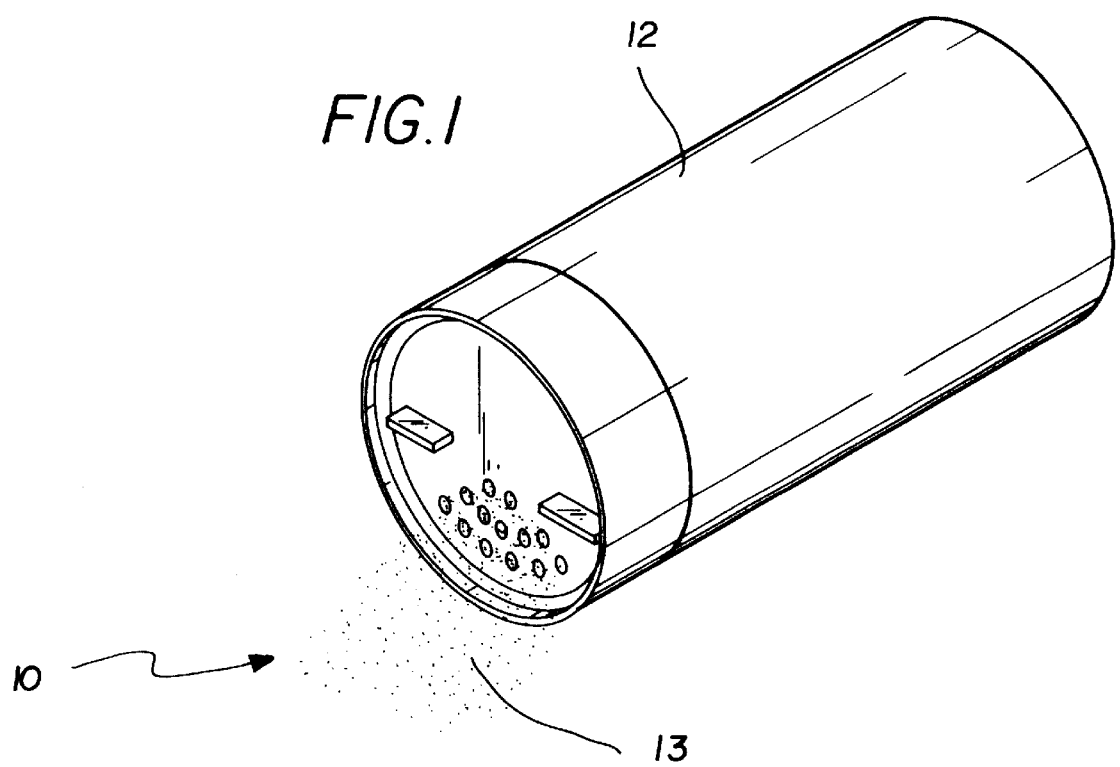
FIG. 1 is a perspective view of a container for dispensing a new pain relief preparation for use while bathing according to the present invention.
Figure 2:
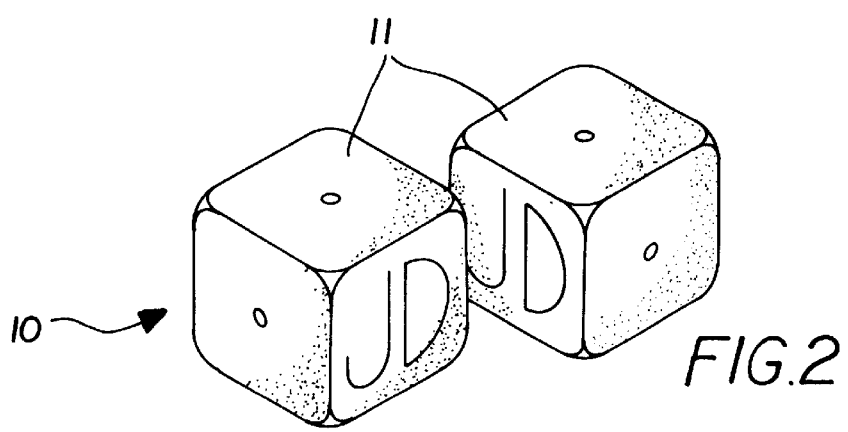
FIG. 2 is a perspective view of cubes formed from the present invention.
Figure 3:
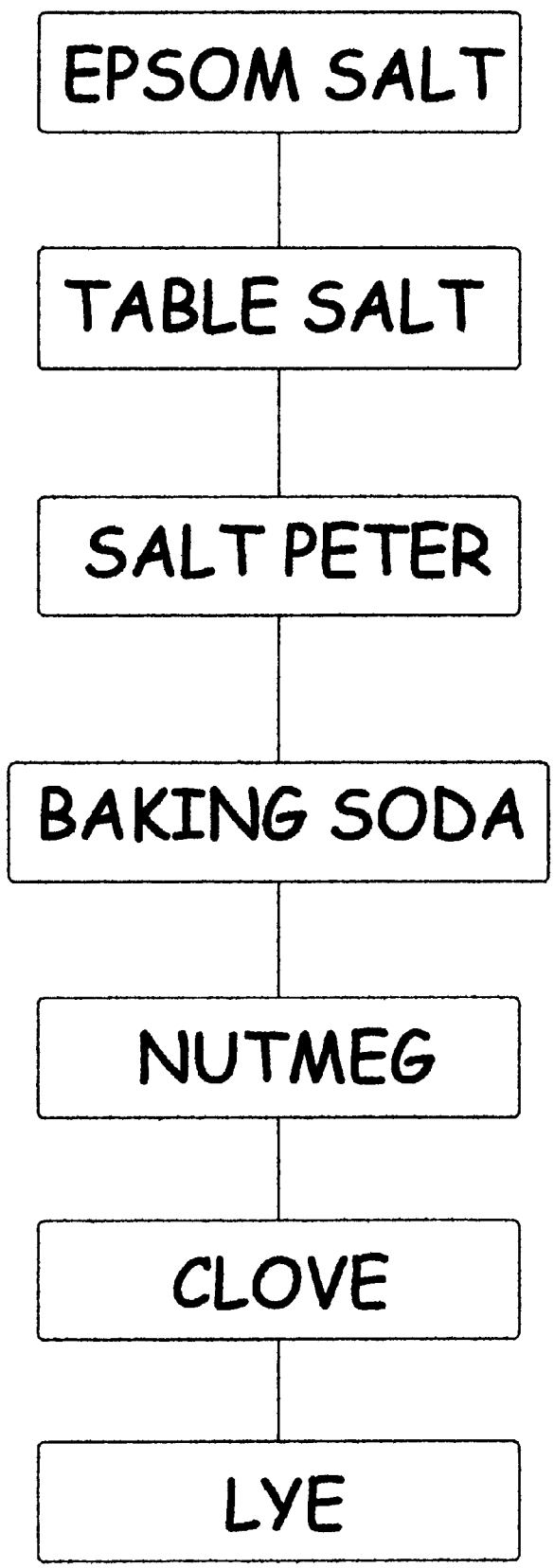
FIG. 3 is a schematic diagram of the components of the present invention.

With reference now to the drawings, and in particular to FIGS. 1 through 3 thereof, a new pain relief preparation for use while bathing embodying the principles and concepts of the present invention and generally designated by the reference numeral 10 will be described.

As best illustrated in FIGS. 1 through 3, the pain relief preparation for use while bathing 10 generally comprises a pain relief preparation for use while bathing comprises (A) salts; (B) sodium bicarbonate; (C) an alkaline solution; (D) a bulb; and (E) aromatic seeds. The pain relief preparation comprises from about 50% to 75% of component (A); from about 15% to 20% of component (B); from about 14% to 20% of component (C);.less than 2% of component (D); and less than 2% of component (E). Component (A) includes Epsom salt, table salt such as sodium chloride, and saltpeter, and component (B) includes sodium bicarbonate, and component (C) includes lye, and component (D) includes clove, and component (E) includes nutmeg. The pain relief preparation includes from about 15% to 21% of the Epsom salt; from about 23% to 30% of the table salt; and from about 15% to 21% of the baking soda. The pain relief preparation also includes about 64 ounces of the Epsom salt; about 96 ounces of the table salt; about 64 ounces of the saltpeter; about 64 ounces of the baking soda; about 60 ounces of the lye; about 2 tablespoons of the clove; and about 2 tablespoons of the nutmeg. The pain relief preparation is formed into a plurality of cubes 11 each being from approximately 4 to 6 ounces and each being adapted to be used with water upon a user's body. The pain relief preparation also can be formed into particles 13 for being dispensed from a container 12. The method of making the pain relief preparation includes using a plastic container and mixing the Epsom salt with the table salt with the saltpeter with the baking soda with the nutmeg and with the clove in the plastic container to form a mixture, and then mixing lye with the mixture, and allowing the mixture to cool, and packaging the mixture into particles 13 and cubes 11 each being approximately 4 to 6 ounces.

One illustrative method of making the pain relief preparation of the invention includes providing a plastic container and mixing in the container a mixture comprising 15% to 21% of Epsom salt, 23% to 30% of table salt, 15% to 21% of saltpeter, 15% to 21% of baking soda, less than 2% of nutmeg, and less than 2% of clove. This mixture is mixed with 14% to 20% of lye. The mixture with the lye is allowed to cool, and then the mixture with the lye may be packaged in the form of particles and cubes each being approximately 4 to 6 ounces.

In use, the user takes the cube and along with water rubs the particles 13 or cube 11 upon one's body, and should allow one's body to air dry rather than using a towel to dry off. This pain relief preparation essentially soothes one's body and virtually takes the aches and pains away.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A pain relief preparation for use while bathing comprises: (A) salts; (B) sodium bicarbonate; (C) clove; and (D) nutmeg, said pain relief preparation comprising from about 50% to 75% of component (A); from about 15% to 20% of component (B); between 0 and 2% of component (C); and between 0 and 2% of component (D); component (A) comprising Epsom salt, sodium chloride, and saltpeter; and component (B) comprising sodium bicarbonate; said pain relief preparation including from about 15% to 21% of said Epsom salt; from about 23% to 30% of said sodium chloride; and from about 15% to 21% of said sodium bicarbonate, said pain relief preparation comprising about 64 ounces of said Epsom salt; about 96 ounces of said sodium chloride; about 64 ounces of said saltpeter; about 64 ounces of said sodium bicarbonate; about 2 tablespoons of said clove in bulb form; and about 2 tablespoons of said nutmeg in seed form, said pain relief preparation being formed into a plurality of cubes each being from approximately 4 to 6 ounces and each being adapted to be used with water upon a user's body.

* * * * *